United States Patent [19]

Kitamori et al.

[11] Patent Number: 4,722,602

[45] Date of Patent: Feb. 2, 1988

[54] APPARATUS AND METHOD FOR ANALYZING PARTICLES IN A MEDIUM

[75] Inventors: Takehiko Kitamori, Hitachi; Kazumichi Suzuki, Mito; Tsuguo Sawada, Kodaira, all of Japan

[73] Assignee: Hitachi, Ltd., Tokyo, Japan

[21] Appl. No.: 894,665

[22] Filed: Aug. 1, 1986

[30] Foreign Application Priority Data

Aug. 14, 1985 [JP] Japan ................. 60-177552

[51] Int. Cl.$^4$ ............................. G01N 21/01
[52] U.S. Cl. ..................... 356/336; 356/432; 356/441
[58] Field of Search ........... 356/432, 432 T, 436, 356/441, 442, 336; 374/5, 45; 73/643, 645, 646

[56] References Cited

U.S. PATENT DOCUMENTS 4,277,179 7/1981 Bruce ........................ 396/433
4,413,504 11/1983 Voigtman et al. ........... 250/432 R

OTHER PUBLICATIONS

Oda et al, "Analysis & Turbid Solutions by Laser-Induced Photoacoustic Spectroscopy" *Analytical Chemistry* vol. 52, (1980) pp. 650-653.

*Primary Examiner*—R. A. Rosenberger
*Attorney, Agent, or Firm*—Fay, Sharpe, Beall, Fagan, Minnich & McKee

[57] ABSTRACT

A medium including particles to be analyzed is contained in a cell through which excitation rays are passed. The excitation rays are focused and have a predetermined wave form. A period in time of the excitation rays is set substantially equal to and preferably longer than the attenuation time of an acoustic pulse which is generated when the excitation rays are absorbed in the particle and when the particle release heat. The acoustic pulse is used to analyze particle size and number of particles.

18 Claims, 8 Drawing Figures

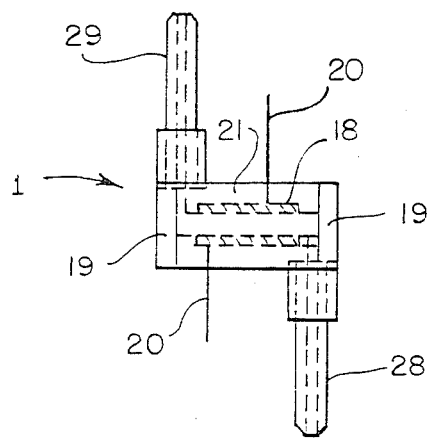
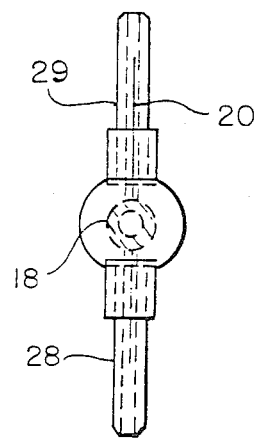
FIG. 6A    FIG. 6B
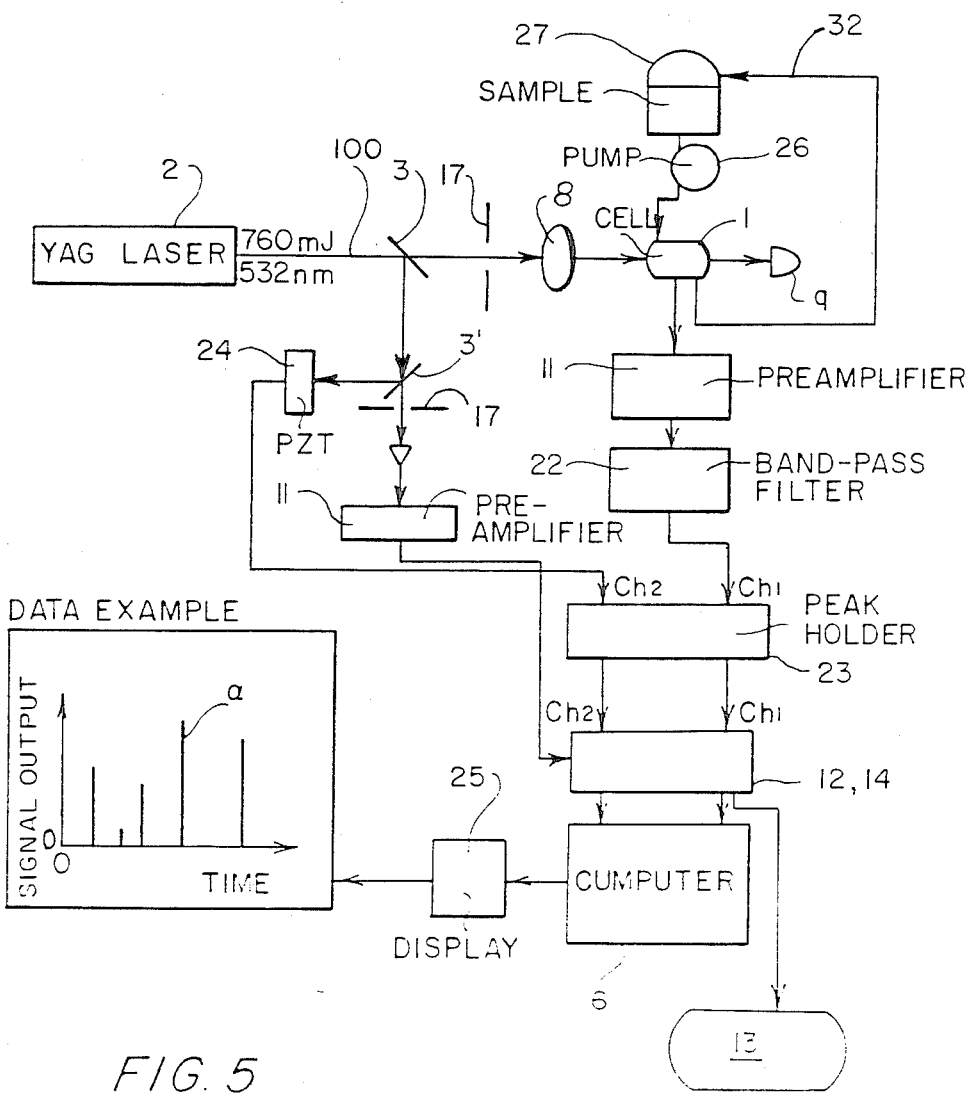
FIG. 5

APPARATUS AND METHOD FOR ANALYZING PARTICLES IN A MEDIUM

FIELD OF THE INVENTION

The present invention relates to an apparatus and method for analyzing particles in a medium, by a photoacoustic spectroscopy, more particularly, analyzing submicron order particles in liquids, for example, trace impurities in reagent water.

BACKGROUND OF THE INVENTION

Oda et al introduced photoacoustic spectroscopy for analyzing particles in water in "Analysis of Turbid Solutions by Laser-Induced Photoacoustic Spectroscopy" in a magazine, *Analytical Chemistry*, Vol. 52, No. 4, April 1980. It is known, for an analysis of particles in a medium, to apply photoacoustic spectroscopy. In the conventional system, the concentration of the particles has been determined. The capability of measuring the particle size distribution is suggested, but it is not practical yet.

SUMMARY OF THE INVENTION

In the present invention, the excitation rays, which are a focused and pulsed beam, are impinged upon particles. The period of the pulsed beam is preferably longer than the attenuation time of an acoustic signal that is generated when the pulsed beam impinges upon a particle. Therefore, each of the acoustic signals corresponds to each of the particles, respectively.

It is an object of the present invention to provide an apparatus and a method that are able to count the number of particles in a medium.

It is another object of the present invention to provide an apparatus and a method that are able to measure particle sizes in a medium.

It is another object of the present invention to provide an apparatus and a method that are able to continuously analyze particles in a flowing medium.

It is another object of the present invention to provide an apparatus and a method that are not affected by Rayleigh Scattering so that it is made to be available to analyze particles of 0.5 $\mu$m or smaller.

It is another object of the present invention to provide an apparatus and a method that are able to break or able to divide particles when the excitation rays impinge upon the particles.

BRIEF DESCRIPTION OF THE DRAWINGS

FIG. 5 shows further details of the embodiment of the present invention.

FIGS. 6A and 6B show a side view and a front view, respectively, of a cell, which is applicable to the embodiment shown in FIGS. 1, 2 and 5.

DETAILED DESCRIPTION

Figure 7:
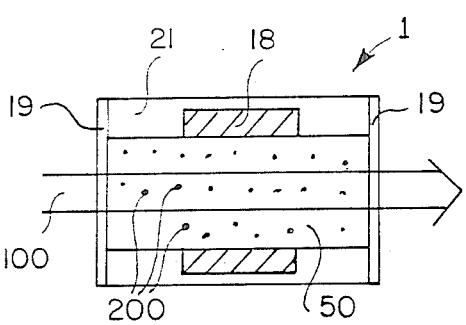
FIG. 7 depicts a comparison of a conventional system and the present invention.

First, a comparison of a conventional system and the present invention about the principle, excitation rays, and photoacoustic signals in photoacoustic spectroscopy is described according to FIG. 7.

A cell 1, in whih a medium 50 is to be analyzed and contained, is constructed as a glass cylinder 21 having an inside surface on which a cylindrical piezoelectric crystal 18 is provided, and at both ends of which optical windows 19 are provided. When an excitation beam 100 passes through the optical window 19 and impinges upon the particles 200 included in the medium 50, the particles 200 absorb the beam 100 and emit heat in a relaxation process. Then, by the heat, the medium 50 near the particles 200 is expanded. The expansion of the medium is changed to acoustic waves, and the acoustic waves are detected as photoacoustic signals by the piezolecyric crystal 18. In this case the nature of the acoustic wave signal does not depend on the kind of excitation beam.

In the conventional system, an excitation beam, the power of which is $10^{-1} \sim 10^{1}$ [w], and modulation frequency of which is $10^{1} \sim 10^{2}$ [HZ], amplitude-modulated to a rectangular wave or sinuosoidal wave 300, is impinged upon the particles in the medium, and a stationary acoustic wave 400 is generated with periodical emission of heat from the particles. In this case, the radius of the excitation beam is fully greater than that of the particles, and the acoustic wave is generated by a pulsation or oscillation of the whole excitation beam passing region caused by the heat from the particles. The heat released into the excitation beam passing region is proportional to the number of atoms and molecules that contribute to the nonradiation excitation and relaxation process, that is, to the concentration of the particles; therefore, the amplitude of the photoacoustic signal is proportional to the concentration of the particles. Further, the time from absorption of the excitation beam by the particles to release of heat into the medium near the particles depends on the particle size; therefore, a phase delay $\phi$ of the photoacoustic signal from the impingement timing of the excitation beam to the particles is effected by the particle size. This means that it is possible to determine the particle size in the conventional system even though it is not so practical.

In the present invention, a focused pulsed beam 500, the power of which is $10^{6} \sim 10^{9}$ [w] and pulse width of which is $10^{0} \sim 10^{1}$ [ns], is used as excitation rays. Therefore, the particles in the beam path are quickly heated. The medium near the particles may be induced to melt, evaporate or even boil if the intensity of the excitation beam is high. The medium adjacent to the particles is locally expanded by the heat released from the particles; then the acoustic pulse is generated. In the present invention, therefore, it is not the whole excitation beam passing region that oscillates, but only the medium adjacent to the particles which becomes a localized sound source; the generated acoustic pulses corespond to the respective particles. Further, the period of the excitation beam is preferably set longer than the attenuation time of the acoustic pulse from a particle; no stationary acoustic wave is generated. Therefore, it is possible to count the particle number by counting the acoustic pulses. Since the peak intensity of the acoustic pulse is proportional to the heat quantity released from the particle and the heat quantity depends on the particle size, the particle size can be determined from the peak intensity. Since the time required to release heat from the particle depends on the particle size, the particle size can be determined from the time delay from the impingement of the excitation beam to the appearance of the peak 600 of the acoustic pulse by the particle.

In the present invention, as in the conventional system, a photoacoustic signal is generated by the light absorption of the medium itself on the optical window. But in the present invention, since the time required to release heat for boiling or evaporation, such as seen in the particles is not needed, the peak 700 of the photoacoustic pulse from the medium appears faster than that of the particles; therefore, they can be easily distinguished and the photoacoustic pulse by the medium itself can be removed from the processed signal, if necessary.

Since the photoacoustic signal generated by soluble matter does not require time to release heat, the photoacoustic signal from the soluble matter appears with the same timing as the acoustic pulse by the medium itself. It is, therefore, possible to determine the quantity or concentration of the soluble matter from the peak intensity of the signal. The signals 800 by reverberation continue within the attenuation time of the photoacoustic pulse after the signal 600.

Generally, the acoustic wave $P(\vec{r}, t)$ generated from a heat source $H(\vec{r}, t)$ can be given as:

$$\Box P(\vec{r}, t) = - \frac{\beta}{Cp} \cdot \frac{\partial}{\partial t} H(\vec{r}, t) \quad (1)$$

wherein $\Box$ is the d'Alembertian differential operator, Cp is the specific heat of the medium, $\beta$ is the isothermal expansion coefficient of the medium. For the acoustic wave generated by the heat source being pulse-like, it suffices that the time dependent member on the right side of the equation (1) is $\delta$-functional. Therefore, for a light irradiation system to the particle to be employed, it suffices if the change of irradiation light intensely with time is $\delta$-functional. For instance, if the spatial distribution $R(\vec{r})$ of the irradiation light is independent of the time distribution $M(t)$ of that, the heat source $H(\vec{r}, t)$ may be given as:

$$H(\vec{r}, t) = R(\vec{r}) \cdot M(t) \quad (2)$$

Therefore, it is merely required that the following equation may be met:

$$H(\vec{r}, t) = R(\vec{r}) \cdot \sqrt{(t)} \quad (3)$$

This equation (3) means that, in the present invention, it is possible to use a step functional change of irradiation light intensity or a rising phase and falling phase of rectangular wave strength modulated light as well as the pulse light described above.

An acoustic wave detector may make use of a piezoelectric effect or optical determination of a density variation or a refraction rate fluctuation of the medium with passage of an acoustic pulse. In the latter case, the output of detection may determine deflection or scattering of the laser beam according to a refraction rate fluctuation.

Figure 1:
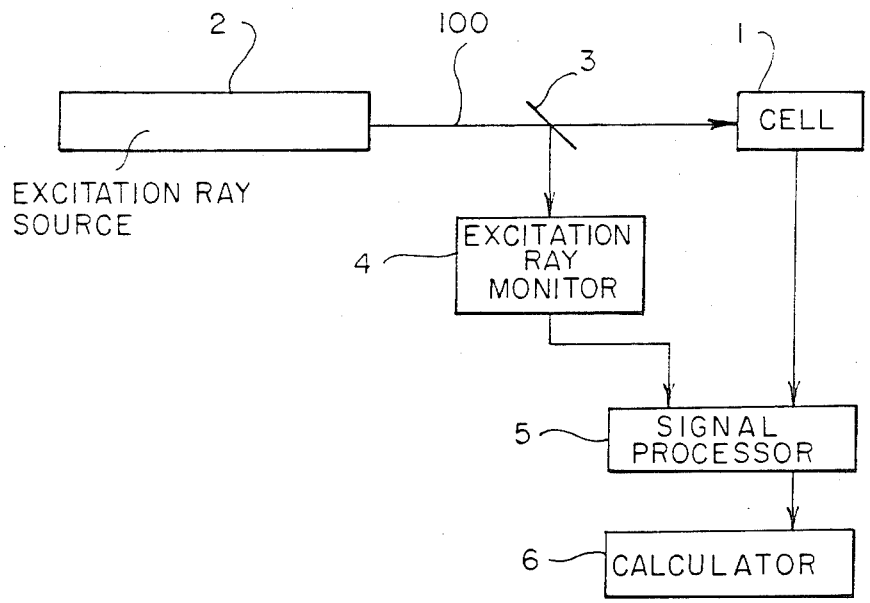
FIG. 1 shows a basic block diagram of the present invention.
Figure 3:
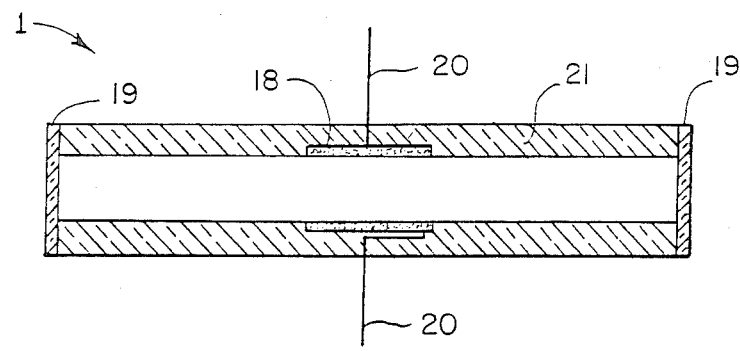
FIG. 3 shows a sectional view of a cell, which is applicable to the embodiment shown in FIGS. 1 and 2.

FIG. 1 shows a basic block diagram of the present invention. A cell 1 contains a medium including particles. An example of the cell 1 is shown in FIG. 3. An excitation ray source 2 generates excitation rays 100 with predetermined form, output power and period in time. A half mirror 3 is placed on the path of the excitation rays from the source 2 to the cell 1 and divides a part of the excitation rays and changes the direction of the divided part. An excitation ray monitor 4 detects the divided excitation rays and outputs a time standard signal when the divided excitation rays are detected. A signal processor 5 is given two signals; one is an acoustic wave output of the cell 1 and the other is the time standard signal from monitor 4. The signal processor 5 detects an acoustic wave form and a delay time from the time standard signal to the peak of the acoustic wave. Calculator 6 processes the outputs of the signal processor statistically and calculates a particle size distribution, if necessary.

According to the basic construction shown in FIG. 1, the present invention is broadly embodied.

Figure 2:
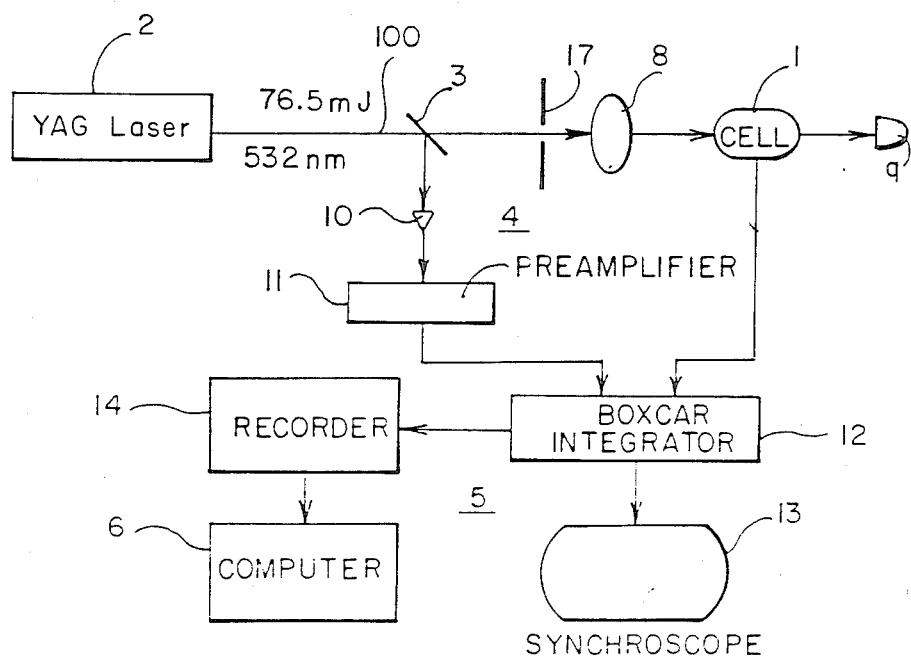
FIG. 2 shows a block diagram of the present invention in more detail.

FIG. 2 shows more detail of the embodiment of FIG. 1. In FIG. 2, means with the same reference numerals shown in FIG. 1 are the same and operate with the same functions described in FIG. 1. An iris diaphragm 17 and the converging lens 8 adjust the average diameter of the excitation beam to be set at a predetermined value. A light absorbing cell 9 is provided to absorb light passed through the cell 1. In FIG. 2, the excitation ray source 2 includes a YAG Laser, which outputs a laser beam 100 having 532 nm of wave length and 76.5 mJ of intensity. The average diameter of the excitation beam in the cell 1 is 28 nm. The excitation ray monitor 4 is constructed as a photodiode 10 and preamplifier 11. The signal processor 5 includes a boxcar integrator 12, a synchroscope 13 and a recorder 14. The boxcar integrator 12 is triggered by the output of the preamplifier 11 and detects a photoacoustic signal from the cell 1. The signal detected by the boxcar integrator 12 is displayed on the synchroscope 13 and is recorded by the recorder 14. A computer is used as the calculator 6.

FIG. 3 shows a sectional view of a batch cell that may be used as the embodiment shown in FIGS. 1 and 2. A cylindrical piezoeffect element 18 is provided on the inside surface of a cylindrical glass 21 and provides two leads 20 to conduct a detected signal to the signal processor 5. One of the optical windows 19 is temporarily removed when the medium to be analyzed is introduced into the cell 1.

Figure 4:
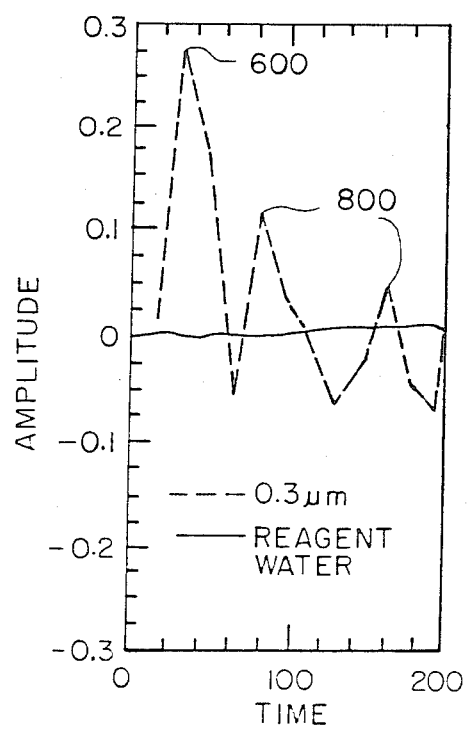
FIG. 4 shows a graph of one example of an analysis by the embodiment shown in FIGS. 1 and 2.

FIG. 4 shows a graph of one example of analysis by the embodiment shown in FIGS. 1 and 2. In this case, the medium is reagent water that does not include particles larger than 0.1 $\mu$m, and in which polystyrene particles 0.3 $\mu$m diameter are added as particles to be detected. In FIG. 4, the first peak 600 is an acoustic signal by a particle, and the continuing two peaks 800 are signals by reverberation of the acoustic signal. From FIG. 4, it is clear to detect the particles of 0.3 $\mu$m by the present invention.

A similar measurement was made of a medium including 0.8 $\mu$m particles with known density and showed the result of 460 counts of acoustic pulses after 2,000 impingements to the medium of the excitation beam. In this case, the particle density is calculated as $3.7 \times 10^3$ particles/ml from the volume of the excitation ray passing region (In this case, the length of the cell 1 is 100 mm.). The result showed good correspondence with the pre-adjusted value $4.0 \times 10^3$ particles/ml.

Further detail of the embodiment is shown in FIG. 5. The cell 1 is specifically shown as a continuous flow through cell, although the batch cell of FIG. 3 may be used. In FIG. 5, a tank 27 is a source of the medium for analyzing particles and feeds a pump 26 to pass the medium to the cell 1. The return pipe 32 may not come back to the tank 27 as shown, but rather the medium may be thrown out. A half mirror 3' is similar to the mirror 3 and reflects a part of light 100 divided from mirror 3 to a piezoelectric effect element that provides a standard signal corresponding the intensity of the received light. An iris diaphragm 17' is similar to the iris diaphragm 17, through which the light passed through the mirror 3' is given to the photodiode 10. A preamplifier 11' is similar to the preamplifier 11 and provides an output signal corresponding to the acoustic wave signal given by the cell 1. A band-pass filter 22 passes only a signal within a predetermined frequency band consistent with the resonance frequency of the cell 1. A peak holder 23 has two channels, ch1 and ch2; one channel keeps a peak intensity of the standard signal given by the piezoelectric effect element 24 and the other channel keeps a peak intensity of the acoustic wave signal given by the band-pass filter 22. A display 25 displays signals processed by the computer 6. An example of the display is shown in FIG. 5 as "Data Example".

The cell 1 is a flow through cell in FIG. 6A and FIG. 6B which show a side view and a front view thereof, respectively. The cell shown in FIGS. 6A and 6B is different only from the one shown in FIG. 3 in that the cell shown in FIGS. 6A and 6B provides an inlet pipe 28 to introduce the medium into the cylindrical glass 21 and an outlet pipe 29 to exhaust the medium from the cylindrical glass 21.

In FIG. 5, the signals which are outputs of the cell 1 and the piezoelectric effect element 24 corresponding to the intensity of the acoustic wave and the excitation rays, respectively, are given to the boxcar integrator 12 through the peak holder 23.

In the case of the cell 1 being a batch cell shown in FIG. 3, it is possible to use a long time for analyzing; then the period for generation of the excitation beam is preferably made longer than an attenuation time of a photoacoustic wave. In the case of the cell 1 being a flow cell shown in FIGS. 6A and 6B, however, the analyzing should be done in as short as possible a time; the period for generation of the excitation beam may be set substantially the same as preferably somewhat less than an attenuation time of a photoacoustic wave so long as it is possible to distinguish individual photoacoustic waves (resulting from individual particles, respectively) from each other. The speed of signal processing in the boxcar integrator may be made higher than that used with the batch cell. The peak holder 23 is useful in the case of the signal processing speed being higher.

In the embodiment as shown in FIG. 5, the standard signal corresponding to the intensity of the excitation rays passed to the cell 1 is available for a normalization or a correction of the intensity of the acoustic wave signal detected by the cell 1.

The intensity of the acoustic wave signal is normalized; in other words, it is changed to the logical value "1" or "0" and it is corrected based upon the detected intensity of the excitation rays before the normalization.

As a further example, an acoustic pulse output of 0.2 mv is gotten for a particle size 0.1 μm; and the number of counts per minute 46 is gotten for a particle density of 100 particles /ml.

It is possible to have a higher sensitivity by employing a resonant absorption of particles in a strong electromagnetic field as known in laser fusion (refer to H. Maki et al, *Journal of the Physical Society of Japan*, 46, 653 (1979)).

Obviously, many modifications and variations of the present invention are possible in light of the above teachings. Thus, it is to be understood that within the scope of the appended claims, the invention may be practiced.

We claim:

1. Apparatus for analyzing particles included in a medium by photoacoustic spectroscopy, comprising:

first means for generating excitation rays that are focused and have a predetermined beam power, a predetermined pulse form, and a predetermined period;

second means for containing the medium which may include the particles to be detected, said second means being placed at a position at which the excitation rays pass in the medium so that photoacoustic signals are generated by heat given off the particles, respectively, when the excitation rays impinge upon the particles;

third means for detecting the photoacoustic signals; and said first means setting the predetermined period substantially equal to or longer than the attenuation time of the photoacoustic signals, so that the number of photoacoustic signals corresponds to the number of particles impinged by the rays.

2. Apparatus in accordance with claim 1, comprising: means for counting the number of the photoacoustic signals detected and producing a signal indicative of the number of particles impinged by the rays.

3. Apparatus in accordance with claim 1, comprising: means for detecting peak values of amplitudes of the photoacoustic signals detected and producing a signal indicative of the size of the particles impinged by the rays.

4. Apparatus in accordance with claim 3, comprising: means for detecting impingement timings of the excitation rays with the particles; and means for detecting time delays of peak positions of the photoacoustic signals from the impingement timings of the excitation rays and producing a signal indicative of the size of the particles impinged by the rays.

5. Apparatus in accordance with claim 3, comprising: means for detecting the intensity of the excitation rays; and means for normalizing in response to both said third means and means for detecting the intensity of the excitation rays.

6. Apparatus in accordance with claim 1, wherein first means generates the excitation rays as a laser beam.

7. Apparatus in accordance with claim 1, wherein said second means has cell means for continuously flowing the medium.

8. Apparatus in accordance with claim 7, wherein said third means is provided along the path of the medium of said cell means.

9. Apparatus in accordance with claim 1, comprising; means for determining the time between the generation of the excitation rays and the detection of the photoacoustic signals, so that the particle size is determined.

10. Apparatus for analyzing a particle included in a medium by photoacoustic spectroscopy, comprising:

first means for generating excitation rays that are focused and have a predetermined beam power, a predetermined pulse form, and a predetermined period;

second means for containing the medium which may include the particles to be detected, said second means being placed at a position at which the excitation rays pass in the medium so that photoacoustic signals are generated by heat given off the particles when the excitation rays impinge upon the particles;

said first means setting focusing and the predetermined period of the rays relative to the attenuation time of the photoacoustic signals so that individual photoacoustic waves resulting from individual particles being impinged by the rays are formed and distinguishable from each other;

third means for individually detecting and distinguishing the photoacoustic signals and producing an output; and means for determining the time between the generation of the excitation rays and the detection of the photoacoustic signals so that the particle size is determined.

11. Apparatus in accordance with claim 10, comprising;

means for detecting intensity of the excitation rays; and means for normalizing the output of said third means in response to said means for detecting intensity of the excitation rays.

12. Apparatus in accordance with claim 10 wherein said second means has a cell means for continuously flowing the medium.

13. Apparatus in accordance with claim 12, wherein said third means is provided along the path of the medium of said cell means.

14. Method for analyzing particles included in a medium by photoacoustic spectroscopy, comprising:

generating excitation rays that are focused and have a predetermined beam power, a predetermined pulse form, and a predetermined period;

containing the medium which may include particles to be detected;

placing the medium in a position at which the excitation rays pass in the medium;

generating photoacoustic signals by heat given off the particles when the excitation rays impinge upon the particles;

detecting the photoacoustic signals generated; and setting the predetermined period of the excitation rays substantially equal to or longer than the attenuation time of the photoacoustic signals, so that the number of photoacoustic signals corresponds to the number of particles impinged by the rays.

15. Method in accordance with claim 14, comprising;

counting the number of the photoacoustic signals and producing a signal indicative of the number of particles impinged by the rays.

16. Method in accordance with claim 14, comprising;

detecting the peak values of the amplitudes of the photoacoustic signals and producing a signal indicative of the size of the particles impinged by the rays.

17. Method in accordance with claim 16, comprising;

detecting time delays of peak positions of the photoacoustic signals from the impingement timings of the excitation rays and producing a signal indicative of the size of the particles impinged by the rays.

18. Method in accordance with claim 16, comprising;

detecting the values of amplitudes of the excitation rays; and normalizing the peak values of amplitudes of the photoacoustic signals based on the values of amplitudes of the excitation rays so that a signal indicative of the number of particles impinged by the rays is produced.

* * * * *